United States Patent
Bai

(10) Patent No.: US 10,892,037 B2
(45) Date of Patent: Jan. 12, 2021

(54) METHODS FOR COMPRESSION OF MOLECULAR TAGGED NUCLEIC ACID SEQUENCE DATA

(71) Applicant: LIFE TECHNOLOGIES CORPORATION, Carlsbad, CA (US)

(72) Inventor: Cheng-Zong Bai, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 234 days.

(21) Appl. No.: 15/979,804

(22) Filed: May 15, 2018

(65) Prior Publication Data

US 2018/0336316 A1 Nov. 22, 2018

Related U.S. Application Data

(60) Provisional application No. 62/507,117, filed on May 16, 2017, provisional application No. 62/517,235, filed on Jun. 9, 2017.

(51) Int. Cl.
G06F 17/00 (2019.01)
G06F 7/00 (2006.01)
(Continued)

(52) U.S. Cl.
CPC ............. *G16B 50/00* (2019.02); *G16B 20/00* (2019.02); *G16B 30/00* (2019.02); *G16B 40/00* (2019.02);
(Continued)

(58) Field of Classification Search
CPC ........ G16B 50/00; G16B 50/50; G16B 40/00; G16B 20/00; G16B 30/00; G16B 30/10; H03M 7/70; C12Q 1/6869
(Continued)

(56) References Cited

U.S. PATENT DOCUMENTS 5,276,868 A * 1/1994 Poole .................. G06F 16/2246
707/693
5,603,022 A * 2/1997 Ng ...................... G06F 16/2246
707/693
(Continued)

FOREIGN PATENT DOCUMENTS

WO 2013/138604 9/2013
WO 2015/083004 6/2015

OTHER PUBLICATIONS

Andrews, T. D. et al., "DeepSNVMiner: a sequence analysis tool to detect emergent, rare mutations in subsets of cell populations", *PeerJ*, vol. 4: e2074; XP055496726; DOI: 10.7717/peerj.2074, May 24, 2016, 13 pp.

(Continued)

*Primary Examiner* — Pavan Mamillapalli
(74) *Attorney, Agent, or Firm* — Carolyn Koenig

(57) ABSTRACT

A method for compressing molecular tagged sequence data includes: grouping sequence reads associated with a molecular tag sequence to form a family of sequence reads, corresponding vectors of flow space signal measurements and corresponding sequence alignments, calculating an arithmetic mean of the corresponding vectors of flow space signal measurements to form a vector of consensus flow space signal measurements, calculating a standard deviation of the corresponding vectors of flow space signal measurements to form a vector of standard deviations, determining a consensus base sequence based on the vector of consensus flow space signal measurements, determining a consensus sequence alignment and generating a compressed data structure comprising consensus compressed data, the consensus compressed data including for each family, the consensus base sequence, the consensus sequence alignment, the vector of consensus flow space signal measurements, the vector of standard deviations and the number of members.

20 Claims, 11 Drawing Sheets

(51) Int. Cl.
  *G16B 50/00* (2019.01)
  *H03M 7/30* (2006.01)
  *G16B 30/00* (2019.01)
  *G16B 40/00* (2019.01)
  *G16B 20/00* (2019.01)
  *G16B 50/50* (2019.01)
  *C12Q 1/6869* (2018.01)
  *G16B 30/10* (2019.01)

(52) U.S. Cl.
  CPC ............... *G16B 50/50* (2019.02); *H03M 7/70* (2013.01); *C12Q 1/6869* (2013.01); *G16B 30/10* (2019.02)

(58) Field of Classification Search
  USPC .......................................................... 707/693
  See application file for complete search history.

(56) References Cited

U.S. PATENT DOCUMENTS

| | | | | |
|---|---|---|---|---|
| 5,678,043 | A * | 10/1997 | Ng | G06F 16/2246 |
| | | | | 707/693 |
| 6,613,563 | B1 * | 9/2003 | Sosnowski | C07K 14/50 |
| | | | | 435/320.1 |
| 7,561,972 | B1 * | 7/2009 | Welch | C12N 15/67 |
| | | | | 702/19 |
| 2005/0032095 | A1 * | 2/2005 | Wigler | C07H 21/04 |
| | | | | 435/6.11 |
| 2013/0090860 | A1 * | 4/2013 | Sikora | G16B 25/00 |
| | | | | 702/20 |
| 2014/0296080 | A1 | 10/2014 | Hubbell et al. | |
| 2015/0299812 | A1 | 10/2015 | Talasaz | |
| 2016/0362748 | A1 | 12/2016 | Mongan et al. | |

OTHER PUBLICATIONS

Balzer, S. et al., "Filtering duplicate reads from 454 pyrosequencing data", *BioInformatics*, vol. 29, No. 7, XP055149282; DOI: 10.1093/bioinformatics/btt047, Feb. 1, 2013, 830-836

Gabriel, C. et al., "Rapid high-throughput human leukocyte antigen typing by massively parallel pyrosequencing for high-resolution allele identification", *Human Immunology*, New York, NY, US, vol. 70, No. 11; XP026698160; DOI: 10.1016/J.HUMIMM.2009.08.009 Aug. 23, 2009, 960-964

Golan, D. et al., "Using state machines to model the Ion Torrent sequencing process and to improve read error rates", *Bioinformatics*, vol. 29, No. 13; XP055158436, Jun. 21, 2013, i344-i351.

PCT/US2018/032655, International Search Report and Written Opinion dated Aug. 14, 2018, 12 pp.

Shugay, M. et al., "MAGERI: Computational pipeline for molecular-barcoded targeted resequencing", *PLOS Computational Biology*, vol. 13, No. 5; DOI: 10.1371/journal.pcbi.100548; XP055496652, May 5, 2017, 1-17.

* cited by examiner

METHODS FOR COMPRESSION OF MOLECULAR TAGGED NUCLEIC ACID SEQUENCE DATA

CROSS-REFERENCE

This application claims the benefit under 35 U.S.C. § 119(e) of U.S. Provisional Application No. 62/507,117, filed May 16, 2017, and U.S. Provisional Application No. 62/517,235, filed Jun. 9, 2017. The entire contents of the aforementioned applications are incorporated by reference herein.

BACKGROUND OF THE INVENTION

Molecular tagging of nucleic acid sequences is useful for identifying the nucleic acid sequence reads that originate from the same polynucleotide molecule and classifying them into a family based on their tag sequence. Large amounts of molecular tagged nucleic acid sequence data, obtained from a nucleic acid sample using various techniques, platforms or technologies, may be stored and processed for variant calling. There is a need for new methods, systems and computer readable media to compress nucleic acid sequence data to reduce memory requirements for storage and improve computational efficiency for variant calling operations, without compromising quality in variant calling.

BRIEF SUMMARY OF THE INVENTION

According to an exemplary embodiment, there is provided a method for compressing molecular tagged nucleic acid sequence data, comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members.

According to an exemplary embodiment, there is provided a non-transitory machine-readable storage medium comprising instructions which, when executed by a processor, cause the processor to perform a method for compressing molecular tagged nucleic acid sequence data, comprising: comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members.

According to an exemplary embodiment, there is provided a system for compressing molecular tagged nucleic acid sequence data, including: a machine-readable memory and a processor configured to execute machine-readable instructions, which, when executed by the processor, cause the system to perform a method for compressing molecular tagged nucleic acid sequence data, comprising: comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
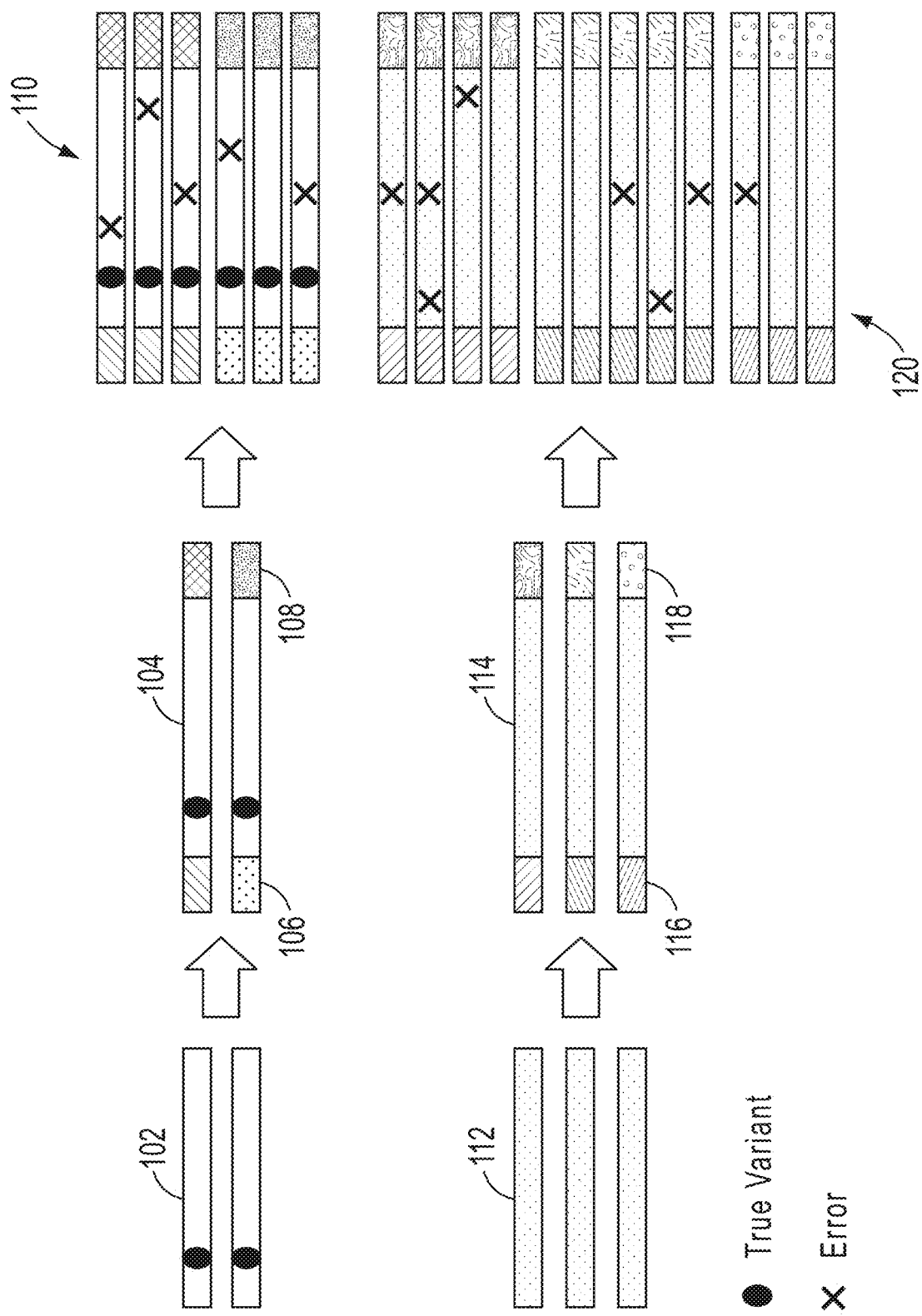
FIG. 1 illustrates an example of molecular tagging where unique molecular tags have been attached to individual polynucleotide molecules followed by PCR amplification and sequencing.

In accordance with the teachings and principles embodied in this application, new methods, systems and non-transitory machine-readable storage medium are provided to compress molecular tagged nucleic acid sequence data to form consensus compressed data for families of nucleic acid sequence reads associated with unique molecular tags. Further teachings provide for detecting variants based on the consensus compressed data.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes.

As used herein, the terms "adapter" or "adapter and its complements" and their derivatives, refers to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "DNA barcode" or "DNA tagging sequence" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

In some embodiments, the disclosure provides for amplification of multiple target-specific sequences from a population of target nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the digesting includes partial digesting of one or more of the target-specific primers from the amplified target sequence. In some embodiments, the amplified target sequences can be ligated to one or more adapters. In some embodiments, adapters can include one or more DNA barcodes or tagging sequences. In some embodiments, amplified target sequences once ligated to an adapter can undergo a nick translation reaction and/or further amplification to generate a library of adapter-ligated amplified target sequences.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

A plurality of defined spaces or reaction confinement regions may be arranged in an array, and each defined space or reaction confinement regions may be in electrical communication with at least one sensor to allow detection or measurement of one or more detectable or measurable parameter or characteristics. This array is referred to herein as a sensor array. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal.

In various embodiments, the phrase "base space" refers to a representation of the sequence of nucleotides. The phrase "flow space" refers to a representation of the incorporation event or non-incorporation event for a particular nucleotide flow. For example, flow space can be a series of values representing a nucleotide incorporation event (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

FIG. 1 illustrates an example of molecular tagging wherein individual polynucleotide molecules have been labeled with unique molecular tags (UMT), amplified in a PCR reaction and sequenced. This example represents the molecular tagging of two tumor variant polynucleotide molecules and three wild type polynucleotide molecules that may be obtained from a cell free DNA (cfDNA) sample. The tumor variant polynucleotide molecule 102 is represented as having a true variant. The wild type polynucleotide molecule 112 does not have the variant. Unique molecular tags attached to each polynucleotide molecule are represented by different patterns for prefix tags 106 and 116 and suffix tags 108 and 118. PCR amplification and sequencing of the tagged tumor variant polynucleotide molecules 104 and tagged wild type polynucleotide molecules 114 may produce multiple amplicons resulting in multiple sequence reads per original tagged polynucleotide molecule. The unique molecular tag is used to identify the sequence reads that originate from the same polynucleotide molecule and classify them into families having the same tag sequence. The tumor variant group of sequence reads 110 shows two families with three amplicons per family, where amplicons in each family share the same unique molecular tag sequences. The wild type group of sequence reads 120 shows three families, where amplicons share the same unique molecular tag sequences, having sizes of four, five and three amplicons, respectively. The number and sizes of families are for illustrative purposes only and are not limiting. The tumor variant sequence reads 110 and wild type sequence reads 120 have errors depicted by X's. These errors may be due to PCR amplification errors or sequencing errors. The errors may be distributed randomly over the sequence reads. In contrast, the true variant should appear in all sequence reads associated with the polynucleotide molecule having the variant.

A family, or molecular family, refers the set of sequence reads having the same unique molecular tags. The family size is the number of sequence reads in the family. A functional family is a family that has a number of members that is greater than a minimum family size. The minimum family size can be any integer value. For example, the minimum family size can be three or greater.

Figure 2:
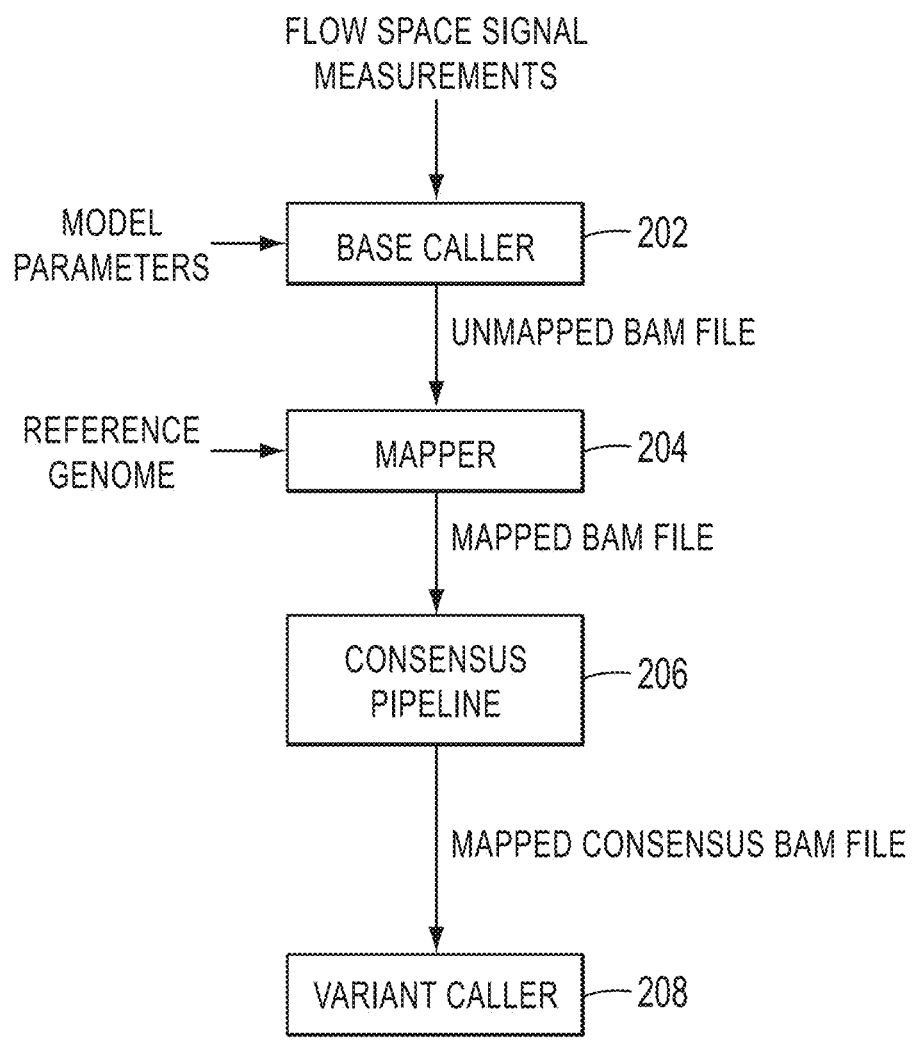
FIG. 2 is a block diagram of an exemplary method for generating consensus compressed data, in accordance with an embodiment.

FIG. 2 is a block diagram of an exemplary method for generating consensus compressed data, in accordance with an embodiment. Flow space signal measurements may be provided to a processor by a nucleic acid sequencing device. In some embodiments, each flow space signal measurement represents a signal amplitude or intensity measured in response to an incorporation or non-incorporation of a flowed nucleotide by sample nucleic acids in microwells of a sensor array. For an incorporation event, the signal amplitudes depend on the number of bases incorporated at one flow. For homopolymers, the signal amplitudes increase with increasing homopolymer length. The processor may apply a base caller 202 to generate base calls for a sequence read by analyzing flow space signal measurements.

Figure 4:
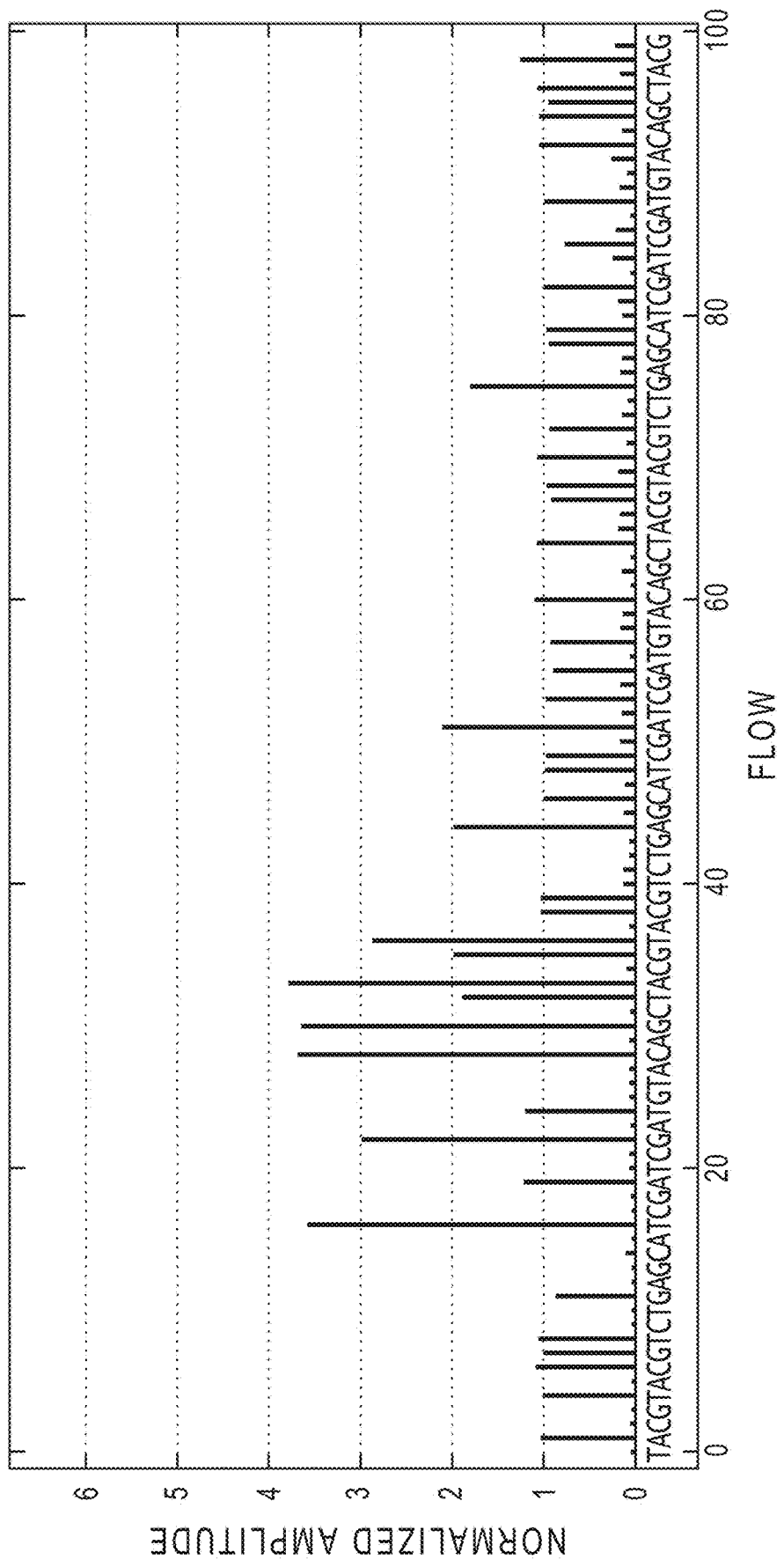
FIG. 4 shows an exemplary representation of flow space signal measurements from which base calls may be made.

FIG. 4 shows an exemplary representation of flow space signal measurements from which base calls may be made. In this example, the x-axis shows the flow number and nucleotide that was flowed in a flow sequence. The bars in the graph show the amplitudes of the flow space signal measurements for each flow from a particular location of a microwell in the sensor array. The flow space signal measurements may be raw acquisition data or data having been processed, such as, e.g., by scaling, background filtering, normalization, correction for signal decay, and/or correction for phase errors or effects, etc. The base calls may be made by analyzing any suitable signal characteristics (e.g., signal amplitude or intensity). The structure and/or design of a sensor array, signal processing and base calling for use with the present teachings may include one or more features described in U.S. Pat. Appl. Publ. No. 2013/0090860, Apr. 11, 2013, incorporated by reference herein in its entirety.

Once the base sequence for the sequence read is determined, the sequence reads may be provided to mapper 204, for example, in an unmapped BAM file. The mapper 204 aligns the sequence reads to a reference genome to determine aligned sequence reads and associated mapping quality parameters. Methods for aligning sequence reads for use with the present teachings may include one or more features described in U.S. Pat. Appl. Publ. No. 2012/0197623, published Aug. 2, 2012, incorporated by reference herein in its entirety. The aligned sequence reads may be provided to the consensus pipeline 206, for example, in a mapped BAM file.

The BAM file format structure is described in "Sequence Alignment/Map Format Specification," Sep. 12, 2014 (https://github.com/samtools/hts-specs), referred to as "BAM specification" herein. As described herein, a "BAM file" refers to a file compatible with the BAM format. As described herein, an "unmapped" BAM file refers to a BAM file that does not contain aligned sequence read information and mapping quality parameters and a "mapped" BAM file refers to a BAM file that contains aligned sequence read information and mapping quality parameters. As described herein, a "consensus" BAM file refers to a BAM file that contains consensus compressed data.

In some embodiments, a read structure for a sequencing read with molecular tagging may include, starting from the 5' end, a library key, a barcode sequence, a barcode adapter, a prefix molecular tag, a sequence template, a suffix molecular tag, and a P1 adapter. Base calling may include trimming the library key, barcode sequence and barcode adapter from the rest of the sequencing read and storing them in the key sequence (KS) tag field of the read group header @RG of the BAM file format. Base calling may include trimming the P1 adapter from the sequencing read and storing it in a comment line @CO of the BAM header.

In some embodiments, the base caller 202 may be configured to detect the tag structure and trim the tag from the sequencing read. Trimmed tags may be stored in the BAM read group header (@RG) in fields for custom tags ZT (for a prefix tag, for example) and YT (for a suffix tag, for example). Since the read group header is associated with the sequencing read data of the template, the integrity of the tag's association with the family group may be maintained. Subsequent mapping or alignment with a reference sequence may be applied to the template sequence without a prefix tag or a suffix tag. This reduces the possibility of erroneous mapping of a portion of a tag to the reference sequence.

In some embodiments, a tag sequence may include a subset of random bases and a subset of known bases. A tag trimming method may require that the sequence of bases in the tag portion of the sequencing read match the known bases. A tag trimming method may select a base string that has a number of bases equal to the known length of a tag. In some embodiments, a tag trimming method may detect and correct sequencing error in the tag, such as insertions and deletions. Correcting sequencing errors in the tag may provide more accurate family identification.

In some embodiments, the mapped BAM file may store a plurality of sequence reads, a plurality of vectors of flow space signal measurements and a plurality of sequence alignments corresponding to the sequence reads. The mapped BAM file may store the vectors of flow space signal measurements in the custom tag field ZM. The mapped BAM file may store the model parameters in the custom tag field ZP. The mapped BAM file may store the molecular tag sequences associated with the sequence reads in the BAM read group header, as described above. The mapped BAM file may be stored in memory and provided to the consensus pipeline 206. In some embodiments, other file formats may be used to store a plurality of sequence reads, a plurality of vectors of flow space signal measurements, a plurality of sequence alignments and molecular tag sequences corresponding to the sequence reads.

Figure 3:
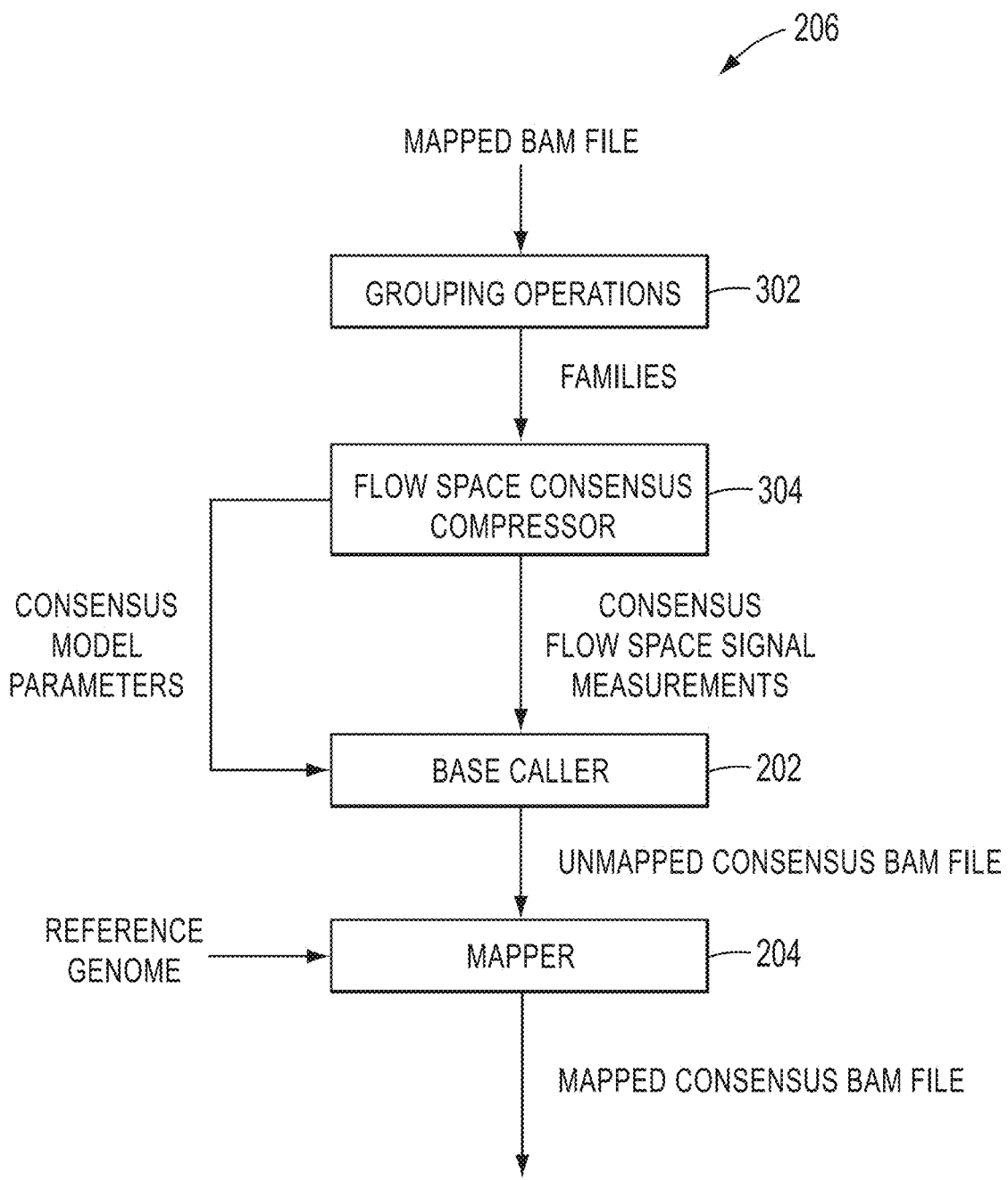
FIG. 3 is a block diagram of an exemplary method for the consensus pipeline 206, in accordance with an embodiment.

FIG. 3 is a block diagram of an exemplary method for the consensus pipeline 206, in accordance with an embodiment. Grouping operations 302 may use the molecular tag sequence information to identify families of sequence reads and corresponding flow space signal measurements. Grouping operations 302 may compare molecular tag sequences associated with the sequence reads and apply a grouping threshold. For example, the criterion of the grouping threshold can require that all tag sequences of members of a group of sequence reads have 100% tag sequence identity. Sequence reads and corresponding flow space signal measurements that are determined to share a common tag sequence, by meeting the criterion of the grouping threshold, are grouped into a given family, where the common tag sequence is unique to that family. Each family will have a number of members which is the number of sequence reads grouped in the family. In some embodiments, families not having at least a minimum number of members will not be further processed and may be removed from memory. Methods for grouping sequence reads based on molecular tag sequences for use with the present teachings may include one or more features described in U.S. Pat. Appl. Publ. No. 2016/0362748, published Dec. 15, 2016, incorporated by reference herein in its entirety.

In some embodiments, the flow space consensus compressor 304 may determine consensus compressed data based on the flow space signal measurements for each of the grouped families as follows:
 a. Calculate an arithmetic mean of the vectors of flow space signal measurements of each grouped family to form a vector of consensus flow space signal measurements for each family.
 b. Calculate a standard deviation of the vectors of flow space signal measurements of each family to form a vector of standard deviations for each family.

In some embodiments, the flow space consensus compressor 304 may receive at least one model parameter corresponding to each vector of flow space signal measurements. The flow space consensus compressor 304 may calculate an arithmetic mean of model parameters of the family to form at least one consensus model parameter for the family. The model parameters may be used for base calling, as described below. In some embodiments, the model parameters may include an incomplete extension (IE) parameter and a carry forward (CF) parameter for each vector of flow space signal measurements. The flow space consensus compressor 304 may calculate an arithmetic mean of the IE parameters and an arithmetic mean of the CF parameters of each family to form a consensus IE parameter and a consensus CF parameter for each family.

In some embodiments, the base caller 202 may be applied to the vector of consensus flow space signal measurements for each family to generate a consensus base sequence for the respective family. The consensus model parameters may be used in applying a model for base calling. For example, a consensus incomplete extension (IE) parameter and a consensus carry forward (CF) parameter for each family may be provided to the base caller 202. The base calling may include one or more features described in U.S. Pat. Appl. Publ. No. 2013/0090860, published Apr. 11, 2013, and/or U.S. Pat. Appl. Publ. No. 2012/0109598, published May 3, 2012, which are all incorporated by reference herein in their entirety. A consensus sequence alignment for the consensus base sequence may be determined by comparing the consensus base sequence to the sequence read in the family having the highest mapping quality. If the consensus base sequence matches the sequence read having the highest mapping quality, the corresponding sequence alignment is selected as the consensus sequence alignment. If the consensus base sequence does not match the sequence read in the family having the highest mapping quality, the mapper 204 may align the consensus base sequence to a reference sequence or a reference genome to determine the consensus sequence alignment. Methods for aligning consensus sequence reads may include one or more features described in U.S. Pat. Appl. Publ. No. 2012/0197623, published Aug. 2, 2012, incorporated by reference herein in its entirety. In some embodiments, about 1% of consensus sequencing reads, on average, may need realignment by the mapper 204.

In some embodiments, the processor may store the consensus compressed data for each family in a compressed data structure in a memory. The consensus compressed data may include the consensus base sequence, the consensus sequence alignment, the vector of consensus flow space signal measurements, the vector of standard deviations and the number of members for each family. The consensus compressed data may further include a set of consensus model parameters for each family. If the family has been separated into flow-synchronized subfamilies, the consensus compressed data may further include the consensus base sequence, the consensus sequence alignment, the vector of consensus flow space signal measurements, the vector of standard deviations and the number of members for each subfamily. In some embodiments, the compressed data structure may be compatible with the BAM file format to produce a mapped consensus BAM file. The BAM specification allows the user to define custom tag fields. For example, custom tag fields may be defined for the BAM file used to store some of the consensus compressed data, as shown in Table 1.

TABLE 1

| BAM Custom Tag Field | DATA |
| --- | --- |
| ZM | Consensus flow space signal measurements |
| ZP | Consensus model parameters |
| ZS | Standard deviations of flow space signal measurements |
| ZR | Number of sequence reads, or members, in family or subfamily |

The original sequence reads, original vectors of flow space signal measurements and original model parameters for each family are not included in the consensus compressed data and may be removed from memory. In some embodiments, the compressed data structure may use a different format protocol than the BAM file format, including custom file formats.

In some embodiments, the compressed data structure, for example the mapped consensus BAM file may be provided to the variant caller 208 of FIG. 2. The variant caller uses the consensus compressed data, rather than the original sequence reads and flow space signal measurements for variant calling, as described below. Methods for variant calling for use with the present teachings may include one or more features described in U.S. Pat. Appl. Publ. No. 2014/0296080, Oct. 2, 2014, incorporated by reference herein in its entirety.

In some embodiments, the base caller 202 applies a model to determine a sequence read from a vector of flow space signal measurements. One such model is represented by the equation:

$$y = Hx + w \quad (1)$$

where, y represents a vector of flow space signal measurements, x represents an ideal flowgram vector, w represents a noise vector, and H is a matrix that represents the model transfer function. The ideal flowgram vector x represents a vector of integer signal values for a given base sequence and a given flow order. The integer signal values correspond to the number of nucleotide incorporations at a particular flow in the flow order. For example, for 1-mer, the ideal flowgram value is 1, for 2-mer, the ideal flowgram value is 2, and for n-mers, the ideal flowgram value is n, etc. For example, given a repeating flow order ACGT and a given base sequence GTCGGA, ideal flowgram vector is [0, 0, 1, 1, 0, 1, 2, 0, 1]. Referring to Table 2, the ideal flowgram vector (column 3) may be constructed from the given base sequence (column 1) and flow order (column 2).

TABLE 2

| BASE SEQUENCE | FLOW ORDER | IDEAL FLOWGRAM VALUE | HARDCLIPPED FLOWGRAM VALUE |
|---|---|---|---|
|  | A | 0 | 0 |
|  | C | 0 | 0 |
| G | G | 1 | 1 |
| T | T | 1 | 1 |
|  | A | 0 | 0 |
| C | C | 1 | 1 |
| GG | G | 2 | 1 |
|  | T | 0 | 0 |
| A | A | 1 | 1 |

The model transfer function represented by the matrix H may be based on an underlying signal model or physical model. The model transfer function may depend on model parameters. In an exemplary model, the model parameters may include phasing parameters, such as an incomplete extension (IE) parameter and a carry forward (CF) parameter. Determining IE and CF parameters are described for use with the present teachings may include one or more features described in U.S. Pat. Appl. Publ. No. 2012/0197623, published Aug. 2, 2012, incorporated by reference herein in its entirety.

Ideally, during nucleotide incorporation, each extension reaction associated with the population of template polynucleotide strands is performing the same incorporation step at the same sequence position in each flow cycle, which can generally be referred to as being "in phase" or in "phasic synchrony" with each other. However, it has been observed that some fraction of template strands in each population may lose or fall out of phasic synchronism with the majority of the template strands in the population. For a family of sequence reads having a common tag sequence, flow-synchronized sequence reads result from the corresponding polynucleotide strands generated from the same polynucleotide molecule incorporating the nucleotide incorporation in phase. Ideally, sequence reads in the same family will have the same flowgram vector. However, it is possible that one or more sequence reads in a family will have a different flowgram vector from the other sequence reads in the family. In this situation, the family may be divided into subfamilies, where each subfamily has matching flow synchronization. Detecting flow synchronization of sequence reads in a family is described further below.

An assumption for the exemplary model described with respect to equation (1) is that the flow-synchronized reads within a family will have the same ideal flowgram vector x. It is also assumed that the noise vector w is a vector of independent identically distributed Gaussian random variables. The arithmetic mean $\bar{y}$ of the vector y of flow space signal measurements, is modeled as follows, $$\bar{y} \triangleq \frac{1}{N}\sum_{n=1}^{N} y_n = \frac{1}{N}\sum_{n=1}^{N} H(IE_n, CF_n)x + w_n = \bar{H}x + \bar{w} \approx H(\overline{IE}, \overline{CF})x + \bar{w} \quad (2)$$

where N is the number of sequence reads in the family, n indicates parameters and vectors corresponding to the $n^{th}$ family member, the overbars indicate arithmetic mean values of the parameters, vector elements and matrix elements. The sequence reads in the family are assumed to be flow-synchronized. The ideal flowgram vector x is assumed to be identical for the flow-synchronized sequence reads in the family, so its mean value is the same. The model transfer function H is approximated by a polynomial expansion as follows, $$[\bar{H}]_{i,j} \triangleq \frac{1}{N}\sum_{n=1}^{N} [H(IE_n, CF_n)]_{i,j} \quad (3)$$

$$= \frac{1}{N}\sum_{n=1}^{N} c_0 + a_1 IE_n + b_1 CF_n + H.O.T.(IE_n, CF_n)$$

$$\approx c_0 + a_1 \overline{IE} + b_1 \overline{CF}$$

$$\approx [H(\overline{IE}, \overline{CF})]_{i,j}$$

where i,j indicate an element of the matrix H and $c_0$, $a_1$, and $b_1$ are coefficients of the expansion. For the exemplary model, the model parameters IE and CF have typical values of less than 1%, so the higher order terms (H.O.T) of the polynomial expansion are insignificant. The above equations (1)-(3) show that the arithmetic mean of the vector of flow space signal measurements and the arithmetic mean of the model parameters corresponding to the sequence reads of the family preserve the useful information for variant calling and base calling. Furthermore, the arithmetic mean of the noise vector w has a reduced noise variance. The mean of the noise may be estimated as a bias by the variant caller 208, thereby mitigating its effect.

In some embodiments, flow synchronization of sequence reads in a family may be determined by analyzing the corresponding flowgram vectors as follows:

a. Generate a flowgram vector for each sequence read in the family, the flowgram vector having integer-valued elements. (See Table 2, column 3)

b. Hard clip the integer-valued elements of the flowgram vector to binary-valued elements, where an element of the hard-clipped flowgram vector $x_b(i)$ is set to 1 when flowgram vector element $x(i) \geq 1$ and $x_b(i)$ is set to 0 when x(i)=0. Any values greater than 1 are associated with homopolymer (HP) lengths, so the hard-clipped flowgram vector is also referred to as a HP-compressed flowgram vector. (See Table 2, column 4)

c. Compare the hard-clipped flowgram vectors within the family.
d. If the hard-clipped flowgram vectors within the family match, the family is flow-synchronized.
e. If the hard-clipped flowgram vectors within the family do not match, divide the family members into subfamilies where each subfamily has matching hard-clipped flowgram vectors.

Figure 5:
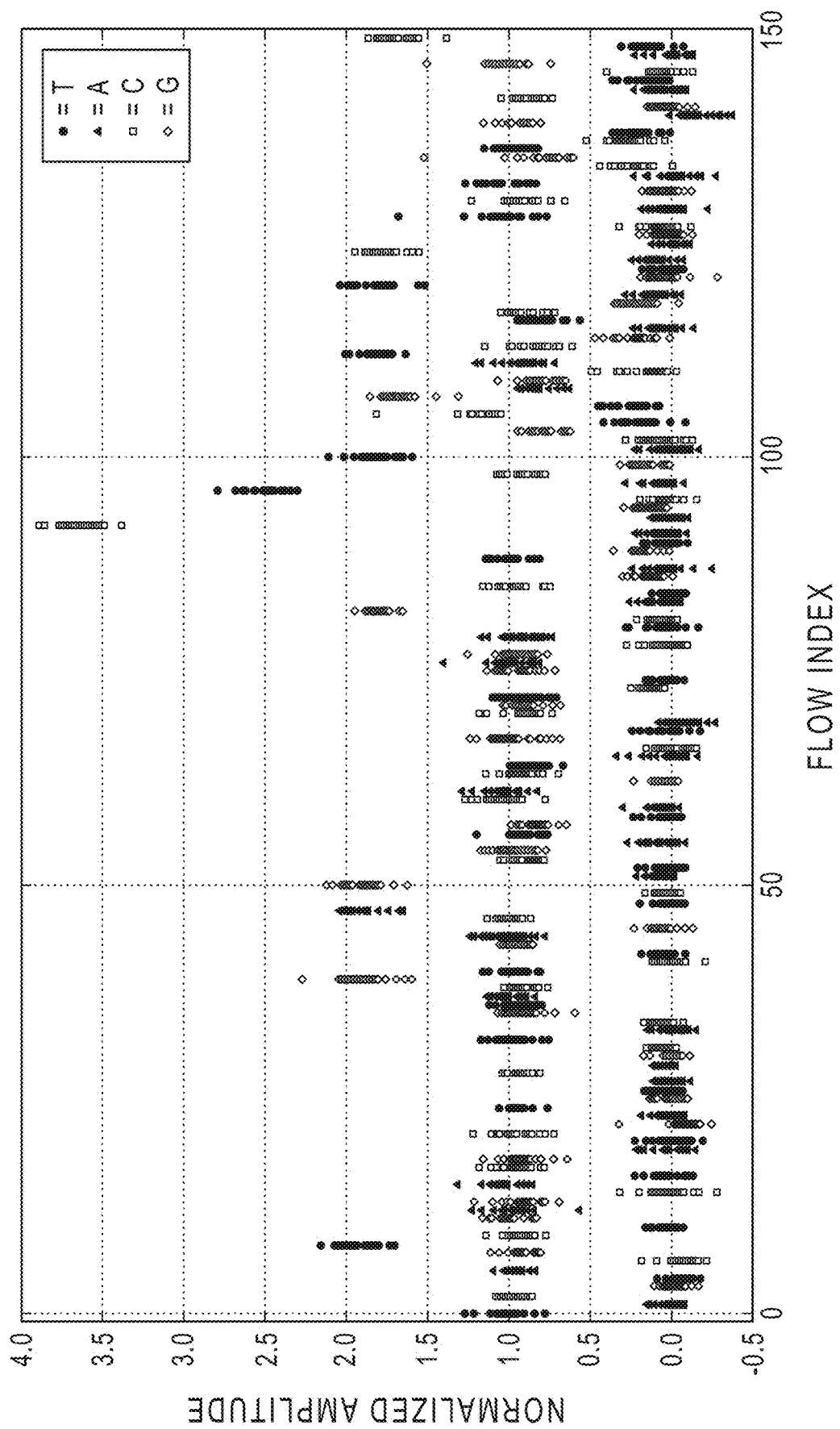
FIG. 5 illustrates an exemplary plot of flow space signal measurements for a single family.

FIG. 5 illustrates an exemplary plot of flow space signal measurements for a single family. The flow index indicates the j-th flow in the flow sequence. The normalized amplitude indicates the value of the flow space signal measurement. The type of plot symbol corresponds to the nucleotide at the particular flow. This plot of flow space signal measurements corresponds to a single flow-synchronized family of sequence reads associated with a common molecular tag. The values of the flow space signal measurements at each flow are clustered near similar values. The flow index corresponds to the element index in the vector of flow space signal measurements. The flow space signal measurements represented in this plot may be input to the flow space consensus compressor 304.

Figure 6:
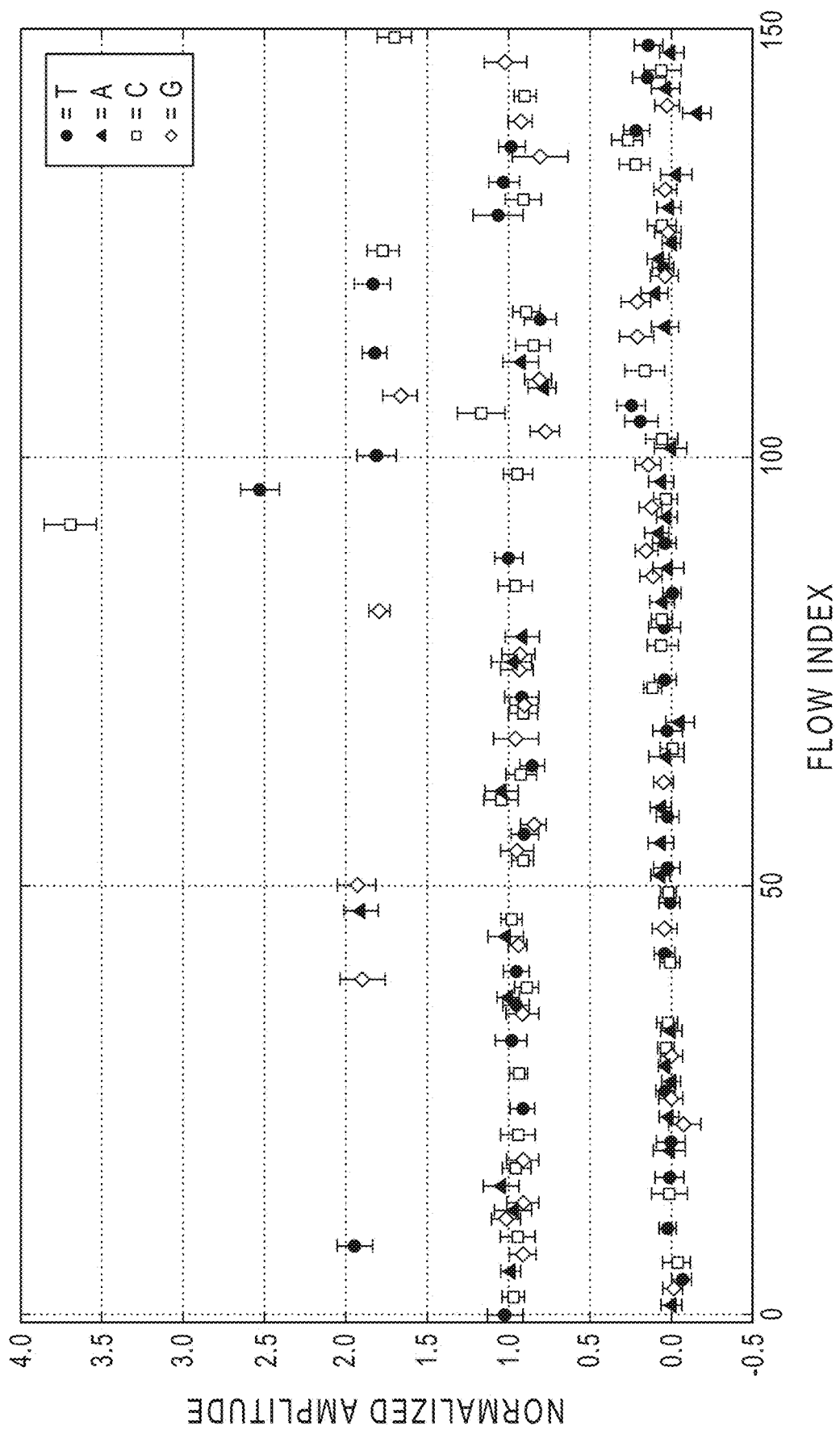
FIG. 6 illustrates an exemplary plot of consensus flow space signal measurements for a single family.

FIG. 6 illustrates an exemplary plot of consensus flow space signal measurements for a single family. This plot shows consensus flow space signal measurement values resulting from consensus calculations on the flow space signal measurements shown in FIG. 5. The plot symbols indicate the arithmetic means that are elements of the vector of consensus flow space measurements for the family. The bars indicate the standard deviations that are elements of the vector of standard deviations for the family.

Figure 7:
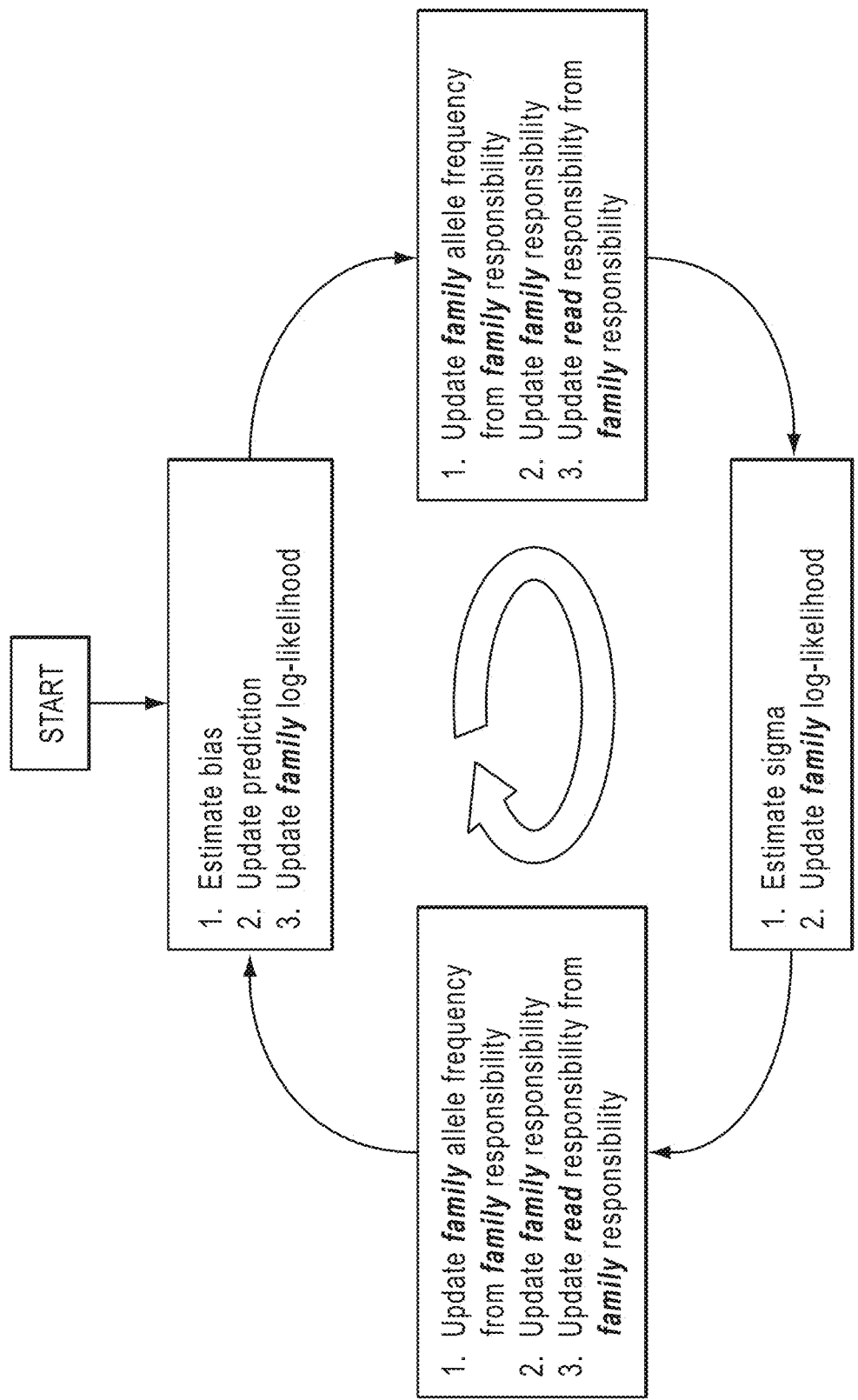
FIG. 7 is a block diagram of an exemplary method of using consensus compressed data for variant calling operations.

FIG. 7 is a block diagram of an exemplary method of using consensus compressed data for variant calling operations. In some embodiments, the variant caller 208 may hypothesize a candidate allele and determine a log-likelihood of a predicted flow space signal value for the candidate allele. The log-likelihood of the predicted flow space signal value corresponding to a given element of the vector of consensus flow space signal measurements is referred to herein as the family log-likelihood. The family log-likelihood may be modeled as a sum of log-likelihoods of original flow space signal measurements $y_n$ where the log-likelihood is based on a non-standardized Student's t distribution, given by the following expression:

$$\sum_{n=1}^{N} \log L(p \mid y_n) = \sum_{n=1}^{N} \alpha - \beta \log\left(1 + \frac{(y_n - p)^2}{\gamma}\right) \quad (4)$$
$$\approx N\left(\alpha - \beta \log\left(1 + \frac{(\bar{y} - p)^2 + \sigma_y^2}{\gamma}\right)\right)$$

where p is the predicted flow space signal value at a given position for the candidate, or hypothesized, allele, $y_n$ is an element at the given position of the $n^{th}$ vector of original flow space signal measurements for the $n^{th}$ member of the family, $\bar{y}$ is the an element at the given position of the vector of consensus flow space signal measurements for the family, $\sigma_y$ is an element at the given position of the vector of standard deviations for the family and N is the number of members in the family. The parameters $\alpha$, $\beta$ and $\gamma$ are based on the degrees of freedom parameter and the scale parameter of the non-standardized Student's t distribution, where $\alpha$ is a function of the degrees of the degrees of freedom and the scale parameter, $\beta$ is a function of the degrees of freedom parameter and $\gamma$ is a function of the degrees of freedom and the scale parameter. The degrees of freedom may be set to a particular value. The scale parameter may be estimated using any suitable method for fitting data to a distribution. In some embodiments, the log-likelihood may be based on other distributions, such as a Gaussian distribution.

In some embodiments, the variant caller 208 may update the prediction by modifying the predicted flow space signal value p so that ($\bar{y}$-p) has a mean value of 0. In some embodiments, log-likelihoods of two candidate, or hypothesized, alleles u and v, are estimated for a decision on which candidate allele is more likely to be present. The variant caller 208 may estimate a bias, where difference $d_j = p_j^u - p_j^v$, is the difference in predicted flow space signal values predicted under the two candidate, or hypothesized, alleles u and v, as follows:

$$\beta_f = \left(\Sigma \frac{d_{ij}^2}{\sigma_{ij}^2}\right)^{-1} * \left(\Sigma \frac{N_i d_{ij}^2 * (\rho_i * (m_{ij} - p_{ij}^u) + (1 - \rho_i) * (m_{ij} - p_{ij}^v))}{\sigma_{ij}^2}\right) \quad (5)$$

where $\beta_f$ is the bias for a forward sequence read, $\sigma_{ij}^2$, is an estimate of the variance for the j-th flow in the i-th consensus read corresponding to the i-th family, $N_i$ is the number of members in the i-th family, $m_{ij}$ is the consensus flow space signal measurement corresponding to the i-th consensus read and the j-th flow index, and $\rho_i$ is the family responsibility for the i-th family. The summations are taken over all consensus reads on the forward strand and all relevant flows. Note that the consensus flow space signal measurement $\bar{y}$ in equation (4) corresponds to $m_{ij}$ where j indicates the j-th element of the vector of consensus flow space signal measurements, $\sigma_y$, in equation (4) corresponds to $\sigma_{ij}$ and i indicates the i-th family. For the reverse bias $\beta_r$, the bias on the reads mapping to the reverse strand may be estimated similarly, except that the sum is then taken over all consensus reads on the reverse strand and all relevant flows. The family responsibility may be estimated by the following expression:

$$\rho_i = \frac{f}{f + (1 - f) * \exp(LL_{vi} - LL_{ui})} \quad (6)$$

where f represents the allele frequency of candidate, or hypothesized, allele u and (1−f) represent the allele frequency of candidate, or hypothesized, allele v, and $LL_{ui}$ and $LL_{vi}$ are log-likelihoods estimated using equation (4), where p, the predicted flow space signal measurement would correspond to candidate allele u in $LL_{ui}$ or to candidate allele v in $LL_{vi}$. The consensus read responsibility can be updated from the family responsibility as follows:

$$\rho_{ni} = \frac{\rho_i}{\rho_i + (1 - \rho_i) * \exp(LL_{vn} - LL_{un})} \quad (7)$$

where $\rho_{ni}$ is the consensus read responsibility for the n-th member of the i-th family and $LL_{un}$ and $LL_{vn}$ are log-likelihoods of the n-th consensus flow space signal measurement for candidate alleles u and v, respectively. In some embodiments, iterations of the estimations and updates for the steps shown in FIG. 7 may be repeated until convergence or repeated for a fixed number of iterations.

In some embodiments, variant calling may use hypothesis testing. For an example of two hypotheses, suppose a candidate, or hypothesized, allele u represents to a reference sequence and a candidate, or hypothesized, allele v, represents a variant sequence. Hypotheses to be tested for the presence of the variant can be expressed by:

$H_{REF}$={Allele Frequency $f \leq$ Minimum Allele Frequency $f_c$}

$H_{VAR}$={Allele Frequency $f >$ Minimum Allele Frequency $f_c$}

The minimum allele frequency $f_c$ may be a parameter set by a user. Applying a maximum a posteriori probability criterion gives the following decisions:

$APP(H_{REF}) \geq APP(H_{VAR})$: $H_{REF}$ is more probable $APP(H_{REF}) < APP(H_{VAR})$: $H_{VAR}$ is more probable where APP indicates the a posteriori probability given the ensemble of read sequences. A quality value, QUAL, for the call is given by, $$QUAL = \min\{APP(H_{REF}), APP(H_{VAR})\} \quad (8)$$

Figure 8:
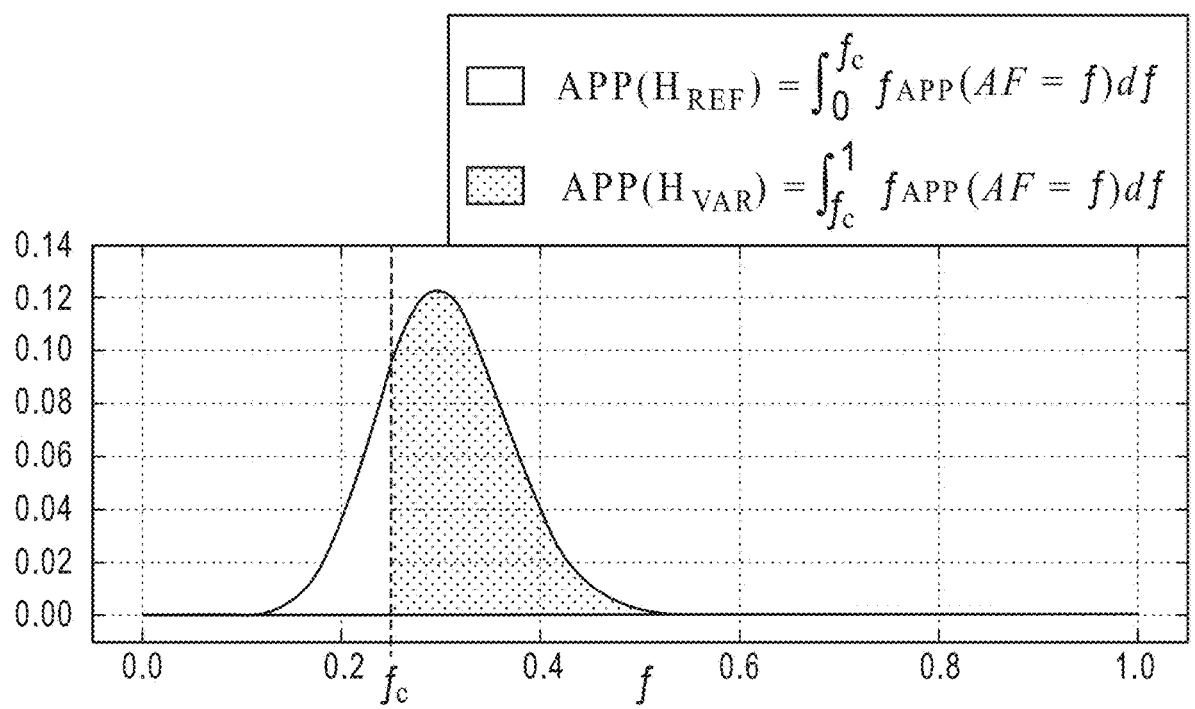
FIG. 8 illustrates an example of a posteriori probabilities $APP(H_{REF})$ and $APP(H_{VAR})$ found by the integrations of equations (9) and (10).

The a posteriori probabilities are given by the expressions:

$$APP(H_{REF}) = \int_0^{f_c} f_{APP}(A=f) df \quad (9)$$

$$APP(H_{VAR}) = \int_{f_c}^1 f_{APP}(AF=f) df \quad (10)$$

where $f_{APP}$ is a posteriori probability density function for allele frequencies AF=f, and $f_c$ is the minimum allele frequency for deciding a variant is present at the location. FIG. 8 illustrates an example of a posteriori probabilities APP ($H_{REF}$) and APP($H_{VAR}$) found by the integrations of equations (9) and (10).

Figure 9A:
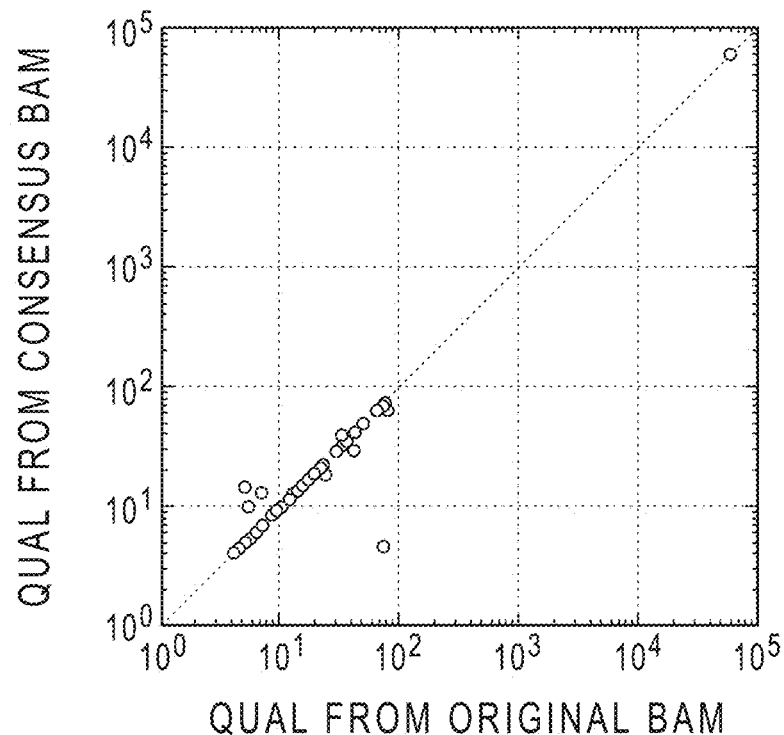
FIG. 9A shows a plot of an exemplary comparison of quality values, QUAL, of variants called using the original data from the mapped BAM file versus consensus compressed data from the mapped consensus BAM file.
Figure 9B:
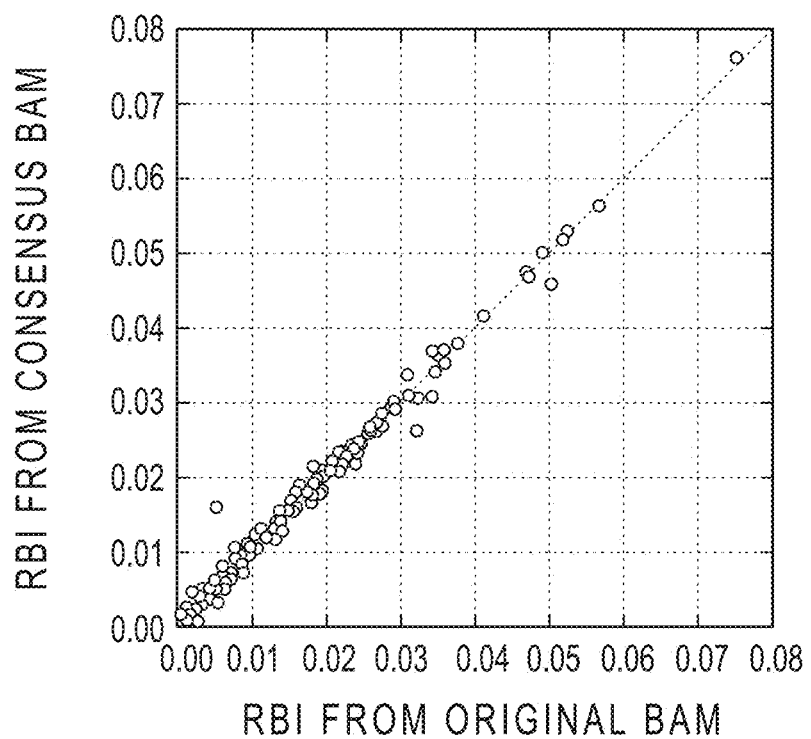
FIG. 9B shows a plot of an exemplary comparison of radius of bias (RBI), estimated using the original data from the mapped BAM file versus consensus compressed data from the mapped consensus BAM file.
Figure 9C:
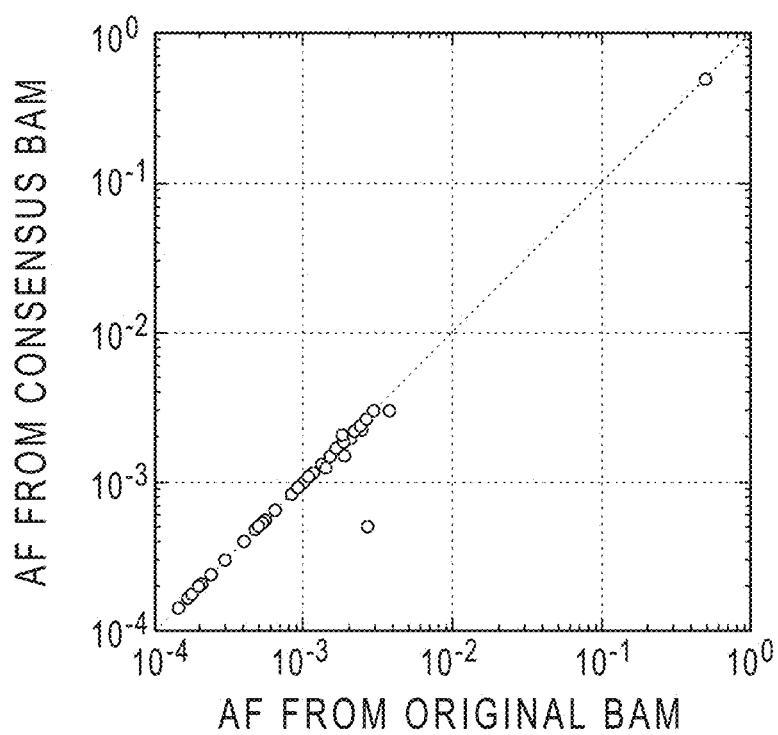
FIG. 9C shows a plot of an exemplary comparison of allele frequencies (AF), of variants called using the original data from the BAM file versus consensus compressed data from the consensus BAM file.

FIGS. 9A, 9B and 9C show exemplary comparisons of results of variant calling based on consensus compressed data from a mapped consensus BAM file and original data from an original mapped BAM file. The mapped consensus BAM file was generated by the consensus pipeline 206 from the original mapped BAM file. Points along the diagonal indicate that the same results for both the consensus compressed data and the original data. FIG. 9A shows a plot of an exemplary comparison of quality values, QUAL, of variants called using the original data from the mapped BAM file versus consensus compressed data from the mapped consensus BAM file. FIG. 9B shows a plot of an exemplary comparison of radius of bias (RBI), estimated using the original data from the mapped BAM file versus consensus compressed data from the mapped consensus BAM file. The RBI is calculated as follows:

$$RBI = SQRT(\beta_f^2 + \beta_r^2) \quad (11)$$

where $\beta_f$ is the forward bias and $\beta_r$ is the reverse bias, as described above. When there are only forward sequence reads, the $\beta_r$ term is omitted in equation (11). FIG. 9C shows a plot of an exemplary comparison of allele frequencies (AF), of variants called using the original data from the BAM file versus consensus compressed data from the consensus BAM file. FIGS. 9A, 9B and 9C show that variant calling results based on consensus compressed data are very similar to variant calling result using the original data. Therefore, using the consensus compressed data has not compromised the quality of the variant calling results.

Table 3 summarizes results of flow space consensus compression for three examples.

TABLE 3

| ITEM | EXAMPLE 1 | EXAMPLE 2 | EXAMPLE 3 |
| --- | --- | --- | --- |
| Number of functional families identified | 102,301 | 270,214 | 1,058,962 |
| Number of sequence reads in the functional families identified | 11,375,156 | 2,380,319 | 11,528,485 |
| Number of consensus sequence reads generated | 122,940 | 306,367 | 2,198,685 |
| Number of consensus sequence reads realigned by mapper 204 | 13,903 | 113,668 | 84,894 |
| Average number of consensus sequence reads per functional family | 1.20175 | 1.13379 | 2.07626 |
| Compression rate | 0.0108078 | 0.128708 | 0.190718 |

The number of functional families identified is a count of the number of families identified by the grouping operations 302 that have a number of members greater than the minimum family size. For example, the functional families may have a family size of three or more members. The number of sequence reads in the functional families identified is a count of all the sequence reads that are members of functional families. The number of consensus sequence reads generated is a count of the total number of consensus reads generated for both families and subfamilies. The number of consensus sequence reads realigned by mapper 204 is a count of consensus reads from both families and subfamilies that were realigned. The average number of consensus sequence reads per functional family is a ratio of the number of consensus sequence reads to the number of functional families. The average number of consensus sequence reads per functional family is an indicator of subfamilies generated per family, e.g. for flow synchronization. The compression rate is calculated by dividing the number of consensus sequence reads by the number of sequence reads in the functional families. The number of consensus sequence reads is proportional to the amount of consensus compressed data and the number of sequence reads in the functional families is proportional to the amount of original read data, so their ratio gives a measure of compression rate.

The compression rates show reduction in the amount of data for the consensus compressed data from the original read data. The compression rates are related to the reduction in the amount of memory required to store the consensus compressed data from the amount of memory required to store the original read data.

Example 1 represents results for unidirectional sequencing and higher amplification. The compression rate is about 0.01. Example 2 represents results for unidirectional sequencing and lower amplification. The compression rate is about 0.13. The average number of consensus reads per functional family is lower than for Example 1. Example 3 represents results for bidirectional sequencing (forward and reverse read directions). For bidirectional sequencing, each family includes at least two subfamilies, one subfamily for forward sequence reads and one family for reverse sequence reads. Other subfamilies may be added for flow synchronization. The compression rate for Example 3 is about 0.19.

The results of Table 3 and of FIGS. 9A-9C show that compression is achieved without compromising variant calling results. The consensus compressed BAM file has smaller memory requirements than the original BAM file. Furthermore, the computational requirements for variant calling using the consensus compressed data are reduced. The computational requirement for variant calling is on the order of M log M operations, where M is the number of sequence reads processed for variant calling. For variant calling using the original sequence reads, M would equal the number of sequence reads in the functional families (see Table 3). For variant calling using the consensus sequence reads, M would equal the number of consensus sequence reads (see Table 3). The reduced computations using the consensus sequence reads result in faster variant calling times.

According to an exemplary embodiment, there is provided a method for compressing molecular tagged nucleic acid sequence data, comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members. The method may further comprise determining whether the sequence reads of the family are flow synchronized. The method may further comprise defining a subfamily of the family based on a matching flow synchronization, wherein the sequence reads of the subfamily are flow synchronized. The method may further comprise performing the steps of calculating an arithmetic mean of the vectors of flow space signal measurements, calculating a standard deviation of the vectors of flow space signal measurements, and determining a consensus base sequence for the sequence reads for the subfamily of the family, wherein the generating a compressed data structure includes consensus compressed data for the subfamily of the family. The step of receiving may further include receiving at least one model parameter corresponding to each vector of flow space signal measurements, wherein the method further comprises calculating an arithmetic mean of the model parameters of the corresponding vectors of flow space signal measurements of the family to form at least one consensus model parameter for the family, wherein the generating the compressed data structure includes the consensus model parameters in the consensus compressed data. The step of determining a consensus base sequence for the sequence reads of the family may be further based on the at least one consensus model parameter for the family. The at least one model parameter may comprise an incomplete extension (IE) parameter. The at least one model parameter may comprise a carry forward (CF) parameter. The method may further comprise determining a variant in a given consensus base sequence using at least a portion of the consensus compressed data from the compressed data structure. The step of determining a variant may be based on the vector of consensus flow space signal measurements and the vector of standard deviations corresponding to the given consensus base sequence. The step of determining a variant may further comprise estimating a log-likelihood of a predicted flow space signal value for a candidate allele based on a function of the consensus flow space signal measurement at a given position in the vector of consensus flow space signal measurements and the standard deviation at the given position in the vector of standard deviations. The compressed data structure may be compatible with a BAM file format. The method may further comprise mapping the consensus base sequence to a reference genome to generate the consensus sequence alignment when the consensus base sequence does not match the sequence read in the family having the highest mapping quality. In such a method, the plurality of nucleic acid sequence reads may comprise forward sequence reads and reverse sequence reads, wherein the step of grouping sequence reads may further comprise identifying two subfamilies for the family, wherein a first subfamily contains the forward sequence reads and a second subfamily contains the reverse sequence reads. The method may further comprise performing the steps of calculating an arithmetic mean of the vectors of flow space signal measurements, calculating a standard deviation of the vectors of flow space signal measurements, and determining a consensus base sequence for the sequence reads for each of the two subfamilies of the family, wherein the generating a compressed data structure includes consensus compressed data for the two subfamilies of the family.

According to an exemplary embodiment, there is provided a non-transitory machine-readable storage medium comprising instructions which, when executed by a processor, cause the processor to perform a method for compressing molecular tagged nucleic acid sequence data, comprising: comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members. The method may further comprise determining whether the sequence reads of the family are flow synchronized. The method may further comprise defining a subfamily of the family based on a matching flow synchronization, wherein the sequence reads of the subfamily are flow synchronized. The method may further comprise performing the steps of calculating an arithmetic mean of the vectors of flow space signal measurements, calculating a standard deviation of the vectors of flow space signal measurements, and determining a consensus base sequence for the sequence reads for the subfamily of the family, wherein the generating a compressed data structure includes consensus compressed data for the subfamily of the family. The step of receiving may further include receiving at least one model parameter corresponding to each vector of flow space signal measurements, wherein the method further comprises calculating an arithmetic mean of the model parameters of the corresponding vectors of flow space signal measurements of the family to form at least one consensus model parameter for the family, wherein the generating the compressed data structure includes the consensus model parameters in the consensus compressed data. The step of determining a consensus base sequence for the sequence reads of the family may be further based on the at least one consensus model parameter for the family. The at least one model parameter may comprise an incomplete extension (IE) parameter. The at least one model parameter may comprise a carry forward (CF) parameter. The method may further comprise determining a variant in a given consensus base sequence using at least a portion of the consensus compressed data from the compressed data structure. The step of determining a variant may be based on the vector of consensus flow space signal measurements and the vector of standard deviations corresponding to the given consensus base sequence. The step of determining a variant may further comprise estimating a log-likelihood of a predicted flow space signal value for a candidate allele based on a function of the consensus flow space signal measurement at a given position in the vector of consensus flow space signal measurements and the standard deviation at the given position in the vector of standard deviations. The compressed data structure may be compatible with a BAM file format. The method may further comprise mapping the consensus base sequence to a reference genome to generate the consensus sequence alignment when the consensus base sequence does not match the sequence read in the family having the highest mapping quality. In such a method, the plurality of nucleic acid sequence reads may comprise forward sequence reads and reverse sequence reads, wherein the step of grouping sequence reads may further comprise identifying two subfamilies for the family, wherein a first subfamily contains the forward sequence reads and a second subfamily contains the reverse sequence reads. The method may further comprise performing the steps of calculating an arithmetic mean of the vectors of flow space signal measurements, calculating a standard deviation of the vectors of flow space signal measurements, and determining a consensus base sequence for the sequence reads for each of the two subfamilies of the family, wherein the generating a compressed data structure includes consensus compressed data for the two subfamilies of the family.

According to an exemplary embodiment, there is provided a system for compressing molecular tagged nucleic acid sequence data, including: a machine-readable memory and a processor configured to execute machine-readable instructions, which, when executed by the processor, cause the system to perform a method for compressing molecular tagged nucleic acid sequence data, comprising: comprising (a) receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads; (b) grouping sequence reads associated with a same molecular tag sequence to form a family of sequence reads, corresponding vectors of flow space signal measurements and corresponding sequence alignments, each family having a number of members; (c) calculating an arithmetic mean of the corresponding vectors of flow space signal measurements to form a vector of consensus flow space signal measurements for the family; (d) calculating a standard deviation of the corresponding vectors of flow space signal measurements to form a vector of standard deviations for the family; (e) determining a consensus base sequence based on the vector of consensus flow space signal measurements for the family; (f) determining a consensus sequence alignment by comparing the consensus base sequence to the sequence read having a highest mapping quality of the corresponding sequence alignments for the family; and (g) generating a compressed data structure comprising consensus compressed data, the consensus compressed data including for each family, the consensus base sequence, the consensus sequence alignment, the vector of consensus flow space signal measurements, the vector of standard deviations and the number of members. The method may further comprise determining whether the sequence reads of the family are flow synchronized. The method may further comprise defining a subfamily of the family based on a matching flow synchronization, wherein the sequence reads of the subfamily are flow synchronized. The method may further comprise performing the steps of calculating an arithmetic mean of the vectors of flow space signal measurements, calculating a standard deviation of the vectors of flow space signal measurements, and determining a consensus base sequence for the sequence reads for the subfamily of the family, wherein the generating a compressed data structure includes consensus compressed data for the subfamily of the family. The step of receiving may further include receiving at least one model parameter corresponding to each vector of flow space signal measurements, wherein the method further comprises calculating an arithmetic mean of the model parameters of the corresponding vectors of flow space signal measurements of the family to form at least one consensus model parameter for the family, wherein the generating the compressed data structure includes the consensus model parameters in the consensus compressed data. The step of determining a consensus base sequence for the sequence reads of the family may be further based on the at least one consensus model parameter for the family. The at least one model parameter may comprise an incomplete extension (IE) parameter. The at least one model parameter may comprise a carry forward (CF) parameter. The method may further comprise determining a variant in a given consensus base sequence using at least a portion of the consensus compressed data from the compressed data structure. The step of determining a variant may be based on the vector of consensus flow space signal measurements and the vector of standard deviations corresponding to the given consensus base sequence. The step of determining a variant may further comprise estimating a log-likelihood of a predicted flow space signal value for a candidate allele based on a function of the consensus flow space signal measurement at a given position in the vector of consensus flow space signal measurements and the standard deviation at the given position in the vector of standard deviations. The compressed data structure may be compatible with a BAM file format. The method may further comprise mapping the consensus base sequence to a reference genome to generate the consensus sequence alignment when the consensus base sequence does not match the sequence read in the family having the highest mapping quality. In such a method, the plurality of nucleic acid sequence reads may comprise forward sequence reads and reverse sequence reads, wherein the step of grouping sequence reads may further comprise identifying two subfamilies for the family, wherein a first subfamily contains the forward sequence reads and a second subfamily contains the reverse sequence reads. The method may further comprise performing the steps of calculating an arithmetic mean of the vectors of flow space signal measurements, calculating a standard deviation of the vectors of flow space signal measurements, and determining a consensus base sequence for the sequence reads for each of the two subfamilies of the family, wherein the generating a compressed data structure includes consensus compressed data for the two subfamilies of the family.

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 10:
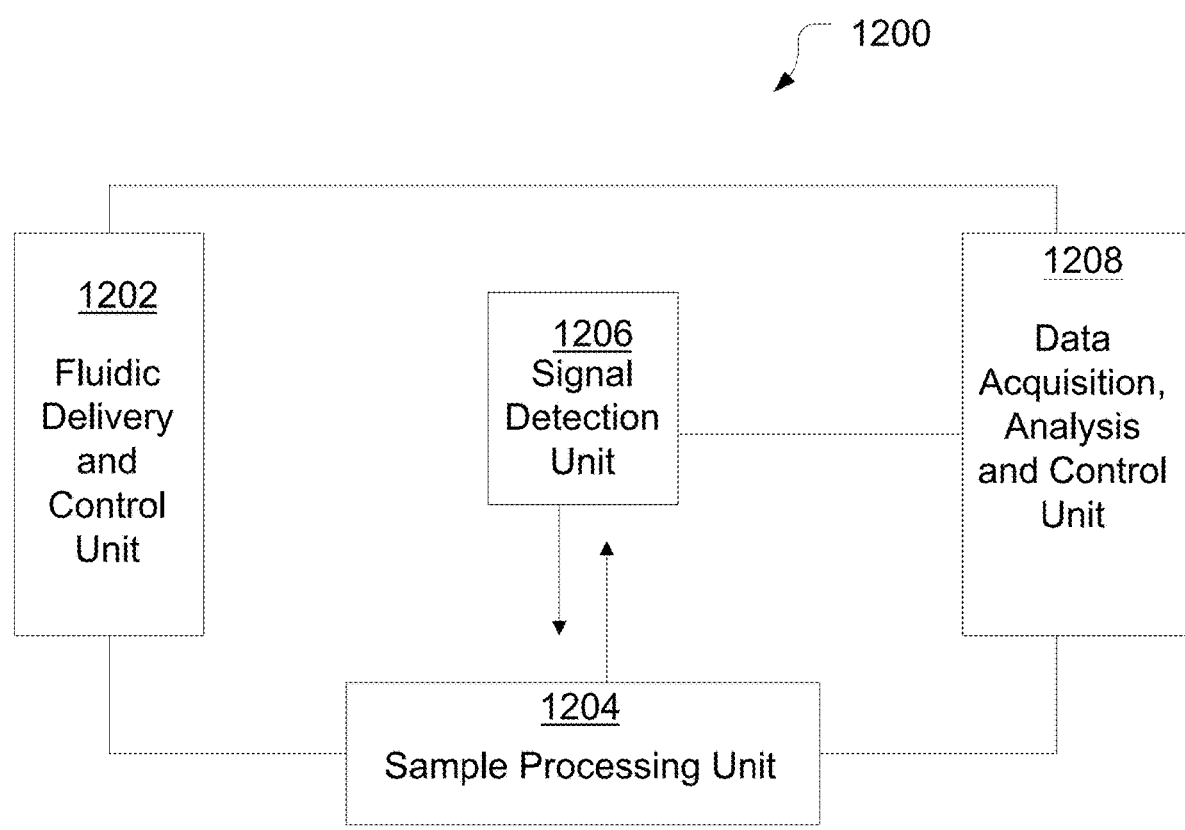
FIG. 10 is a block diagram of an exemplary system for nucleic acid sequencing, in accordance with an embodiment.

Various embodiments of nucleic acid sequencing platforms, such as a nucleic acid sequencer, can include components as displayed in the block diagram of FIG. 10. According to various embodiments, sequencing instrument 1200 can include a fluidic delivery and control unit 1202, a sample processing unit 1204, a signal detection unit 1206, and a data acquisition, analysis and control unit 1208. Various embodiments of instrumentation, reagents, libraries and methods used for next generation sequencing are described in U.S. Patent Application Publication No. 2009/0127589 and No. 2009/0026082. Various embodiments of instrument 1200 can provide for automated sequencing that can be used to gather sequence information from a plurality of sequences in parallel, such as substantially simultaneously.

In various embodiments, the fluidics delivery and control unit 1202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 1204 can include a sample chamber, such as flow cell, a substrate, a micro-array, a multi-well tray, or the like. The sample processing unit 1204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 1206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 1206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 1206 can include optics for the transmission of light from an illumination source to the sample or from the sample to the imaging or detection sensor. Alternatively, the signal detection unit 1206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 1208 can monitor various system parameters. The system parameters can include temperature of various portions of instrument 1200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 1200 can be used to practice variety of sequencing methods including ligation-based methods, sequencing by synthesis, single molecule methods, nanopore sequencing, and other sequencing techniques.

In various embodiments, the sequencing instrument 1200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 1200 can obtain the sequence information from a single nucleic acid molecule or from a group of substantially identical nucleic acid molecules.

In various embodiments, sequencing instrument 1200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for compressing molecular tagged nucleic acid sequence data, comprising:
   receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads;
   grouping sequence reads associated with a same molecular tag sequence to form a family of sequence reads, corresponding vectors of flow space signal measurements and corresponding sequence alignments, each family having a number of members;
   calculating an arithmetic mean of the corresponding vectors of flow space signal measurements to form a vector of consensus flow space signal measurements for the family;
   calculating a standard deviation of the corresponding vectors of flow space signal measurements to form a vector of standard deviations for the family;
   determining a consensus base sequence based on the vector of consensus flow space signal measurements for the family;
   determining a consensus sequence alignment by comparing the consensus base sequence to the sequence read having a highest mapping quality of the corresponding sequence alignments for the family;
   generating a compressed data structure comprising consensus compressed data, the consensus compressed data including for each family, the consensus base sequence, the consensus sequence alignment, the vector of consensus flow space signal measurements, the vector of standard deviations and the number of members; and
   determining a variant in a given consensus base sequence using at least a portion of the consensus compressed data from the compressed data structure.

2. The method of claim 1, further comprising determining whether the sequence reads of the family are flow synchronized.

3. The method of claim 1, further comprising defining a subfamily of the family based on a matching flow synchronization, wherein the sequence reads of the subfamily are flow synchronized.

4. The method of claim 3, further comprising performing the steps of calculating an arithmetic mean of the vectors of flow space signal measurements, calculating a standard deviation of the vectors of flow space signal measurements, and determining a consensus base sequence for the sequence reads for the subfamily of the family, wherein the generating a compressed data structure includes consensus compressed data for the subfamily of the family.

5. The method of claim 1, wherein the receiving further includes receiving at least one model parameter corresponding to each vector of flow space signal measurements, wherein the method further comprises calculating an arithmetic mean of the model parameters of the corresponding vectors of flow space signal measurements of the family to form at least one consensus model parameter for the family, wherein the generating the compressed data structure includes the consensus model parameters in the consensus compressed data.

6. The method of claim 5, wherein the determining a consensus base sequence for the sequence reads of the family is further based on the at least one consensus model parameter for the family.

7. The method of claim 5, wherein the at least one model parameter comprises an incomplete extension (IE) parameter.

8. The method of claim 5, wherein the at least one model parameter comprises a carry forward (CF) parameter.

9. The method of claim 1, wherein the determining a variant is based on the vector of consensus flow space signal measurements and the vector of standard deviations corresponding to the given consensus base sequence.

10. The method of claim 1, wherein the determining a variant further comprises estimating a log-likelihood of a predicted flow space signal value for a candidate allele based on a function of the consensus flow space signal measurement at a given position in the vector of consensus flow space signal measurements and the standard deviation at the given position in the vector of standard deviations.

11. The method of claim 1, wherein the compressed data structure is compatible with a BAM file format.

12. The method of claim 1, comprising mapping the consensus base sequence to a reference genome to generate the consensus sequence alignment when the consensus base sequence does not match the sequence read in the family having the highest mapping quality.

13. The method of claim 1, wherein the plurality of nucleic acid sequence reads comprise forward sequence reads and reverse sequence reads, wherein the grouping sequence reads further comprises identifying two subfamilies for the family, wherein a first subfamily contains the forward sequence reads and a second subfamily contains the reverse sequence reads.

14. The method of claim 13, further comprising performing the steps of calculating an arithmetic mean of the vectors of flow space signal measurements, calculating a standard deviation of the vectors of flow space signal measurements, and determining a consensus base sequence for the sequence reads for each of the two subfamilies of the family, wherein the generating a compressed data structure includes consensus compressed data for the two subfamilies of the family.

15. A non-transitory machine-readable storage medium comprising instructions which, when executed by a processor, cause the processor to perform a method for compressing molecular tagged nucleic acid sequence data, comprising:
   receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads;
   grouping sequence reads associated with a same molecular tag sequence to form a family of sequence reads, corresponding vectors of flow space signal measurements and corresponding sequence alignments, each family having a number of members;
   calculating an arithmetic mean of the corresponding vectors of flow space signal measurements to form a vector of consensus flow space signal measurements for the family;
   calculating a standard deviation of the corresponding vectors of flow space signal measurements to form a vector of standard deviations for the family;
   determining a consensus base sequence based on the vector of consensus flow space signal measurements for the family;
   determining a consensus sequence alignment by comparing the consensus base sequence to the sequence read having a highest mapping quality of the corresponding sequence alignments for the family;
   generating a compressed data structure comprising consensus compressed data, the consensus compressed data including for each family, the consensus base sequence, the consensus sequence alignment, the vector of consensus flow space signal measurements, the vector of standard deviations and the number of members; and
   determining a variant in a given consensus base sequence using at least a portion of the consensus compressed data from the compressed data structure.

16. The non-transitory machine-readable storage medium of claim 15, further comprising instructions which cause the processor to perform the method, wherein the receiving further includes receiving at least one model parameter corresponding to each vector of flow space signal measurements, wherein the method further comprises calculating an arithmetic mean of the model parameters of the corresponding vectors of flow space signal measurements of the family to form at least one consensus model parameter for the family, wherein the generating the compressed data structure includes the consensus model parameters in the consensus compressed data.

17. The non-transitory machine-readable storage medium of claim 15, further comprising instructions which cause the processor to perform the method, further comprising defining a subfamily of the family based on a matching flow synchronization, wherein the sequence reads of the subfamily are flow synchronized.

18. The non-transitory machine-readable storage medium of claim 15, wherein the plurality of nucleic acid sequence reads comprise forward sequence reads and reverse sequence reads, wherein the grouping sequence reads further comprises identifying two subfamilies for the family, wherein a first subfamily contains the forward sequence reads and a second subfamily contains the reverse sequence reads.

19. The non-transitory machine-readable storage medium of claim 15, wherein the compressed data structure is compatible with a BAM file format.

20. A system for compressing molecular tagged nucleic acid sequence data, comprising:
   a machine-readable memory; and
   a processor configured to execute machine-readable instructions, which, when executed by the processor, cause the system to perform a method for compressing molecular tagged nucleic acid sequence data, comprising:
   receiving a plurality of nucleic acid sequence reads, a plurality of vectors of flow space signal measurements and a plurality of sequence alignments, wherein each sequence read is associated with a molecular tag sequence, the molecular tag sequence identifying a family of sequence reads resulting from a particular polynucleotide molecule in a nucleic acid sample, wherein each vector of flow space signal measurements and each sequence alignment correspond with one of the sequence reads;
   grouping sequence reads associated with a same molecular tag sequence to form a family of sequence reads, corresponding vectors of flow space signal measurements and corresponding sequence alignments, each family having a number of members;
   calculating an arithmetic mean of the corresponding vectors of flow space signal measurements to form a vector of consensus flow space signal measurements for the family;
   calculating a standard deviation of the corresponding vectors of flow space signal measurements to form a vector of standard deviations for the family;
   determining a consensus base sequence based on the vector of consensus flow space signal measurements for the family;
   determining a consensus sequence alignment by comparing the consensus base sequence to the sequence read having a highest mapping quality of the corresponding sequence alignments for the family;
   generating a compressed data structure comprising consensus compressed data, the consensus compressed data including for each family, the consensus base sequence, the consensus sequence alignment, the vector of consensus flow space signal measurements, the vector of standard deviations and the number of members; and
   determining a variant in a given consensus base sequence using at least a portion of the consensus compressed data from the compressed data structure.

* * * * *